United States Patent [19]
Ljungmann

[11] Patent Number: 5,580,414
[45] Date of Patent: Dec. 3, 1996

[54] APPARATUS FOR AUTOMATIC APPLICATION OF COVER SLIPS ON MICROSCOPE SLIDES

[76] Inventor: Oystein H. Ljungmann, Elgfaret 15, N-1404 Siggerud, Norway

[21] Appl. No.: 454,206
[22] PCT Filed: Dec. 10, 1993
[86] PCT No.: PCT/NO93/00188
   § 371 Date: Aug. 2, 1995
   § 102(e) Date: Aug. 2, 1995
[87] PCT Pub. No.: WO94/14097
   PCT Pub. Date: Jun. 23, 1994
[51] Int. Cl.⁶ ............................ G02B 21/34; B32B 17/00
[52] U.S. Cl. .................... 156/363; 156/364; 156/556; 156/572; 156/578
[58] Field of Search ............................ 156/362, 556, 156/572, 578, 570, 363, 364

[56] References Cited

U.S. PATENT DOCUMENTS

| | | | |
|---|---|---|---|
| 3,833,449 | 9/1974 | Johnson | 156/556 |
| 3,930,928 | 1/1976 | Tapert | 156/572 |
| 4,033,809 | 7/1977 | Tipton | 156/572 |
| 4,171,241 | 10/1979 | Henderson et al. | 156/572 |
| 4,428,793 | 1/1984 | Sato et al. | 156/572 |
| 4,455,188 | 6/1984 | Stormby | 156/363 |

Primary Examiner—Geoffrey L. Knable
Attorney, Agent, or Firm—Samuels, Gauthier, Stevens & Reppert

[57] ABSTRACT

An apparatus for automatically attaching cover slips (27) to microscope slides (26) having specimens for microscopic examination, including a first magazine (1) receiving a plurality of slides (26), a means (10) for feeding one slide (26) at a time from the magazine (1) to a station (32) for application of adhesive, and a means (34) for placing a cover slip on a slide provided with adhesive. Further, the apparatus includes an additional magazine (3) arranged next to the slides magazine (1) and arranged to receive a stack (36) of cover slips (27), a slide means (10) arranged for reciprocating movement and provided with means (28, 33) for simultaneous feeding of a slide (26) and a cover slip (27) from the respective magazines (1, 3) to an advanced position next to each other at the adhesive application station (32), and for subsequent return of the slide with attached cover slip to the slides magazine, and a means (34) which, provided that a cover slip (27) has been fed to the advanced position, provides for application of adhesive to the slide (26) and thereafter lifting, transfer and pressing-down of the cover slip (27) onto the slide.

11 Claims, 6 Drawing Sheets

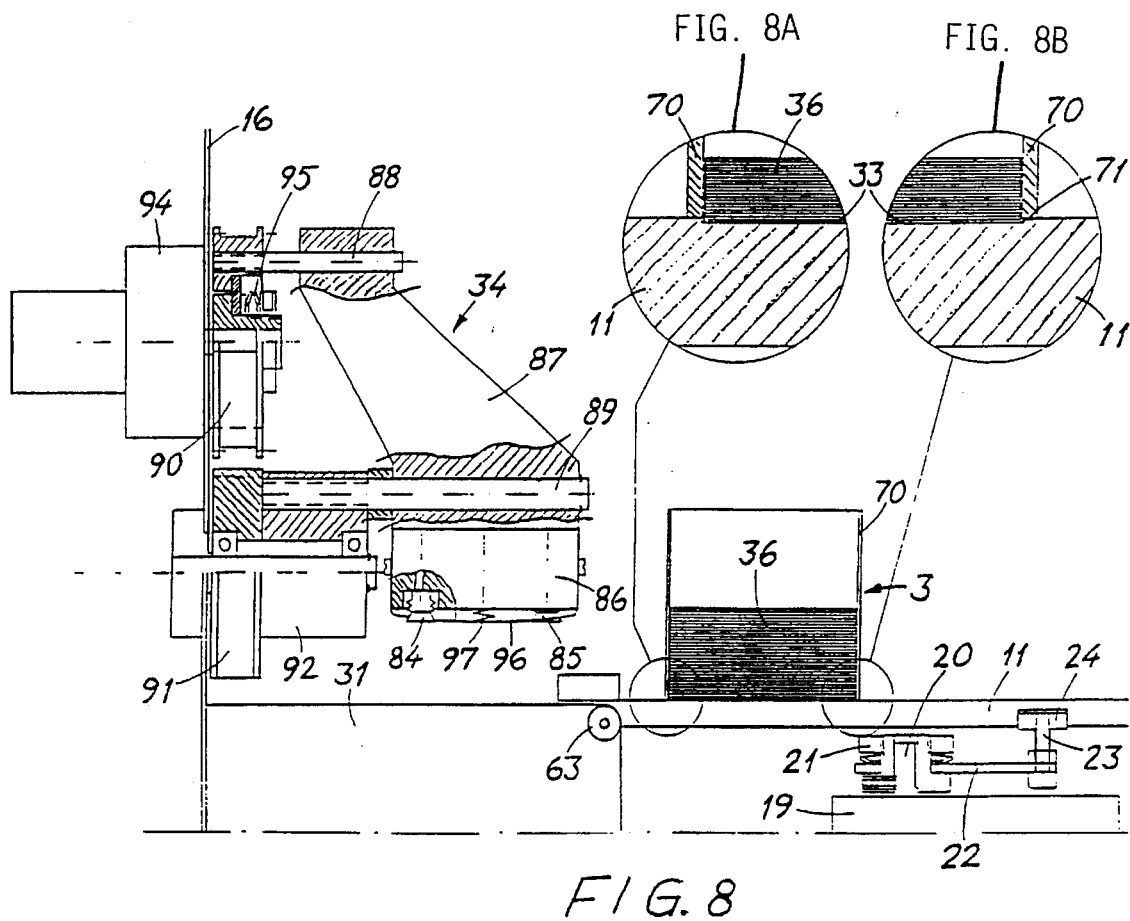
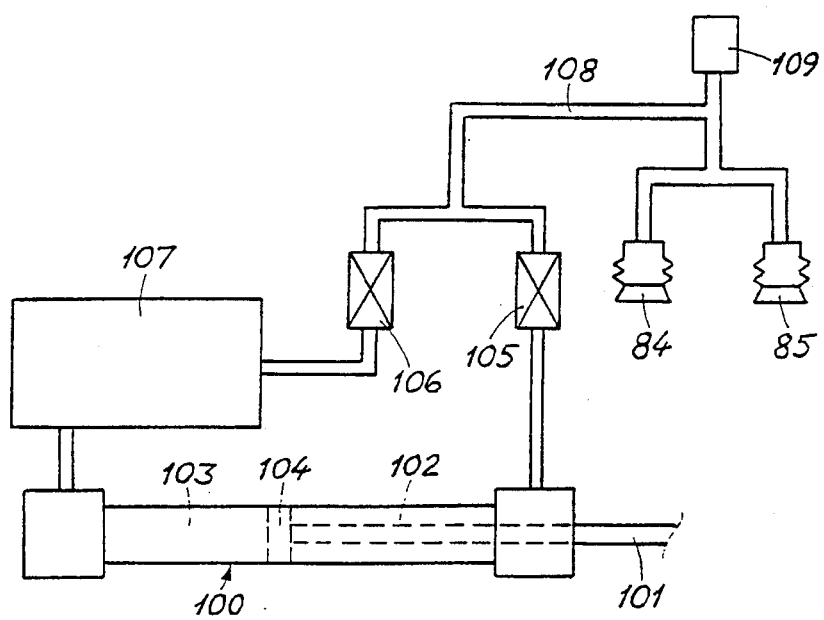

APPARATUS FOR AUTOMATIC APPLICATION OF COVER SLIPS ON MICROSCOPE SLIDES

BACKGROUND OF THE INVENTION

The present invention relates to an apparatus for automatically attaching cover slips to microscope slides having specimens for microscopic examination, comprising a first magazine receiving a plurality of slides, a means for feeding one slide at a time from the magazine to a station for application of adhesive, a means for placing a cover slip on a slide provided with adhesive, and a means for removing the slide with attached cover slip from the station.

Such application of cover slips or cover glasses on microscope slides especially is carried out in hospitals and in medical laboratories, wherein microscope slides having different types of medical specimens, such as cut specimens, cytologic smears, etc. must be covered by protective cover slips. This work was previously, and is partly even now, carried out manually, and it is then a tedious and strenuous work. In many cases it is necessary that the specimens are kept wet by means of a solvent, such as xylene, which is miscible with the adhesive used. The use of such a solvent is, however, injurious to health and represents an environmental risk, since it is harmful to the respiration and is absorbed by the body by skin contact. It is therefore strongly desirable that this work be taken over by apparatus which is able to carry out the work automatically.

There are previously known different types of apparatus for application of cover slips on microscope slides having specimens for microscopy, and as examples of prior art in the field reference may be made to the U.S. Pat. Nos. 3,480,504, 3,930,928 and 4,455,188. The latter patent specification discloses an apparatus of the type stated in the introduction. This apparatus is based on the use of cover slips of plastics, there being provided a supply spool on which there is wound a cover strip ribbon of e.g. plastic foil, and this ribbon is advanced to an application station at which the ribbon is cut into suitable lengths which are successively applied to and pressed together with associated microscope slides. The use of plastics as a cover material has, however, the drawback that scratches easily arise in the plastics, and this results in optical errors in the analysis of specimens on microscope slides which are covered by plastic material.

In addition to the above-mentioned weakness in the use of a plastic material, it has been found that many of the known apparatus and machines for the present purpose either are encumbered with functional faults and therefore are less reliable than desired, or that they have a too small capacity relative to the investment cost.

SUMMARY OF THE INVENTION

It is therefore an object of the invention to provide a fully automatic apparatus which is safe and reliable in operation, and which has a relatively large capacity.

A further object is to provide such an apparatus which is simple to operate and which also gives a good product in terms of quality, which product is suitable for microscopy and for prolonged storage.

For the achievement of the above-mentioned objects there is provided an apparatus of the introductorily stated type which, according to the invention, is characterized in that it comprises an additional magazine arranged next to the slides magazine and arranged to receive a stack of cover slips, a slide means arranged for reciprocating movement and provided with means for simultaneous feeding of a slide and a cover slip from the respective magazines to a position next to each other at the adhesive application station, and for subsequent return of the slide with attached cover slip to the slides magazine, and a means which, provided that a cover slip has been fed to said position, provides for application of adhesive to the slide and thereafter lifting, transfer and pressing-down of the cover slip onto the slide.

An advantageous embodiment of the apparatus is characterized in that the slides magazine comprises at least one cassette which is slidable along vertical guide rails, the cassette being of the type containing mutually spaced slides placed above each other, and being provided along a side wall with a number of teeth for cooperation with a means for downward movement of the cassette in steps corresponding to the distance between the slides. In this embodiment it is advantageous that the feeding means of the slide means for slides comprises a sensing means for sensing whether a slide is present in the topical position in the cassette, and which, in case of a lacking slide, actuates a switch causing return of the slide means to the initial position and one step moving-down of the topical cassette.

In the apparatus according to the invention, the two magazines for slides and cover slips are arranged next to each other, and by means of the special slide means the same drive unit may be used for feeding of slides as well as cover slips. In addition, the slide means sees to it that each slide with attached cover slip is brought back to the same magazine, and more specifically to its original place in the magazine, or in the cassette when a cassette is used as done in the above-mentioned embodiment. This may be an essential advantages in practice, for obtaining easier identification of the specimen glasses and therewith a simplified handling and a higher security against confusion of the specimens.

BRIEF DESCRIPTION OF THE DRAWINGS

The invention will be further described below in connection with an exemplary embodiment with reference to the drawings, wherein

FIG. 8 shows a partly sectioned side view of the fetching means in the intermediate position, and also a sectional side view of the cover-slips magazine and of two enlarged details thereof;

FIG. 9 illustrates the construction of the pneumatic system of the fetching means.

DESCRIPTION OF THE PREFERRED EMBODIMENT(S)

It will be appreciated that, in the present description and in the claims, the word "slide" is used in two different meanings. Thus, in the term "microscopic slide", a slide is a normally rectangular small plate, normally of glass, for the support of a specimen for microscopic examination, whereas in the term "slide means", a slide generally is a sliding or slidable element.

Figure 1:
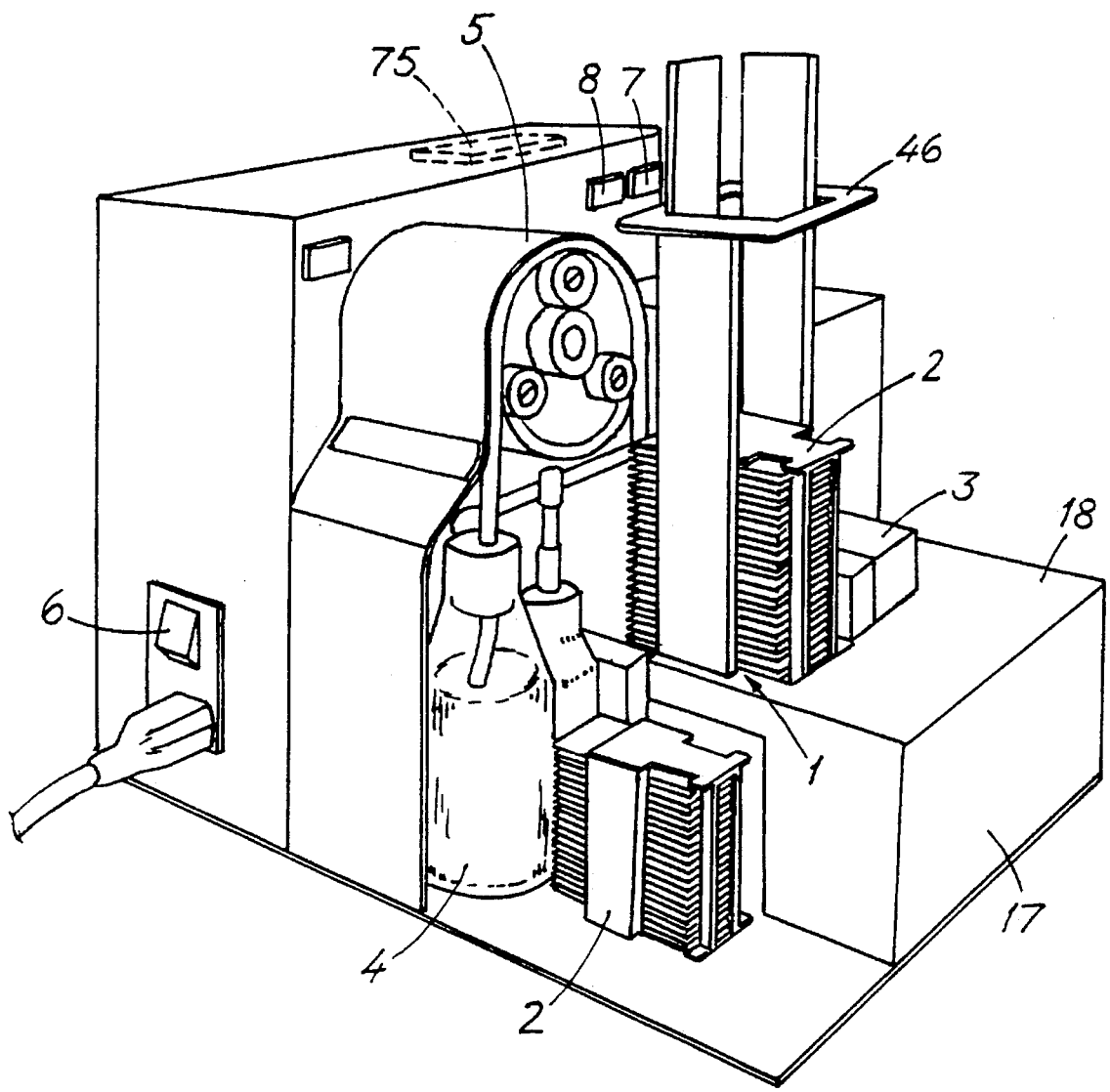
FIG. 1 is a perspective view showing the fundamental construction of an apparatus according to the invention.

From the perspective view in FIG. 1 there appear only some of the main elements of the apparatus according to the invention, viz. a magazine 1 for receiving a number of cassettes 2 for microscope slides, a cover-slips magazine 3, an adhesive supply in the form of a bottle 4 for adhesive, e.g. glue, and a pump means 5 for the supply of adhesive from the bottle 4 to slides at an adhesive application station (not shown). The apparatus is electrically driven, and in FIG. 1 there are shown a main switch 6 and a starting switch 7, and in addition a red warning lamp 8 the function of which will be further described later.

Figure 2:
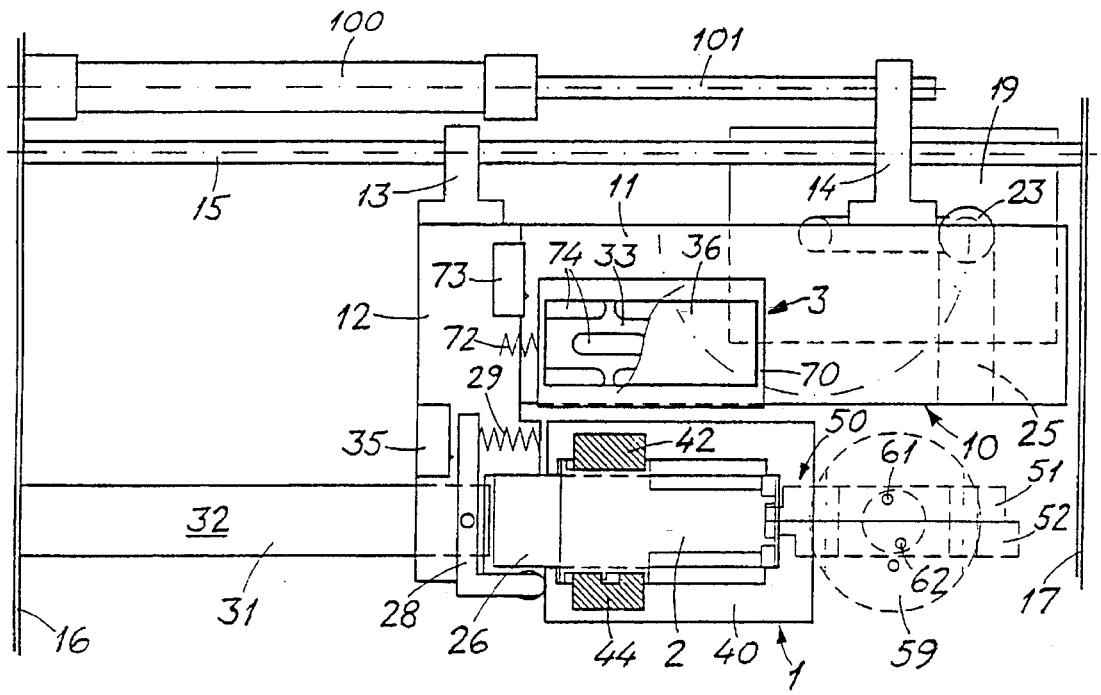
FIG. 2 shows a schematic plan view of the part of the apparatus containing the two magazines and the slide means, some members and elements being omitted for the sake of survey, and wherein the slide means is shown in its initial position.
Figure 3:
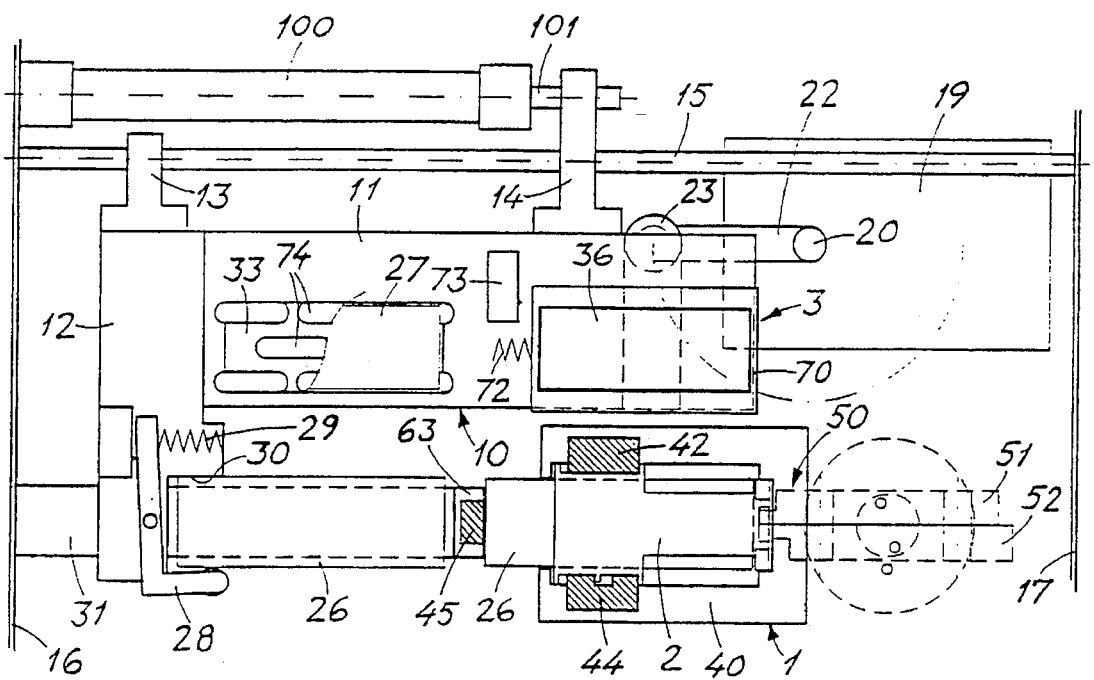
FIG. 3 shows a plan view corresponding to FIG. 2, wherein the slide means is shown in its advanced position.

FIGS. 2 and 3 show schematic plan views of that part of the apparatus which comprises the slides magazine 1, the cover-slips magazine 3 and the slide means 10 of the apparatus. At the left side of these figures, the means at the adhesive application station and the fetching means for cover slips are omitted for the sake of the survey. The slide means 10 comprises a slide plate 11 to which there is fastened a sliding arm 12, and which, by means of a pair of bearing holders 13, 14 with slide bearings, is slidably mounted on a guide shaft 15 extending between a pair of end walls 16, 17 forming part of the case or housing 18 (FIG. 1) of the apparatus. The slide means 10 is reciprocated between an initial or "home" position (shown in FIG. 2) and an advanced or "out" position (shown in FIG. 3), and for such movement of the slide there is provided a reversible slide motor 19 having a driving shaft 20 which, through a friction coupling 21 (see FIG. 8), a driving arm 22 and a pivot 23 having a ball bearing 24, is coupled to a transversely extending groove 25 in the underside of the slide plate 11. By means of this arrangement, the slide means is driven back and forth with a sine operation giving a smooth acceleration and deceleration in the starting and stopping phase, respectively.

As appears from FIGS. 2 and 3, the slides magazine 1 and the cover-slips magazine 3 are arranged next to each other, and the slide plate 11 and the sliding arm 12 are provided with means for simultaneous gripping and feeding of a microscope slide 26 and a cover slip 27 from the respective magazines when the slide means 10 is moved from the initial position in FIG. 2 to the advanced position in FIG. 3. Thus, on the sliding arm 12, there is rotatably mounted a clamping arm 28 which, by means of a spring 29 and in cooperation with an abutment edge 30 on the sliding arm 12, grips a slide 26 and pulls the slide out from the magazine 1 when the slide means is moved from the initial position. During the advancing movement, the sliding arm 12 and the microscope slide 26 slide along a sliding rest 31 forward to the adhesive application station 32. Further, the slide plate 11 is provided with a recess 33 which is suitably dimensioned for receiving a cover slip 27 from the cover-slips magazine 3 when the slide means 10 is in the initial position, and this cover slip is carried along by the slide plate 11 so as to be located in the correct position under the fetching means 34 (see FIG. 8) when the slide means is in the advanced position and the microscope slide is placed at the adhesive application station 32. The cooperation between the recess 33 and the cover-slips magazine 3 will be further described in connection with the description of the cover-slips magazine.

The slides magazine 1 comprises a guide element 40 which is fixed relative to the apparatus housing 18, and vertical guide rails for slidable guiding of cassettes 2 receiving a number of microscope slides 26. As appears from FIG. 4, the guide rails include an inner guide rail 42 which is fastened to the guide element 40 and at its lower end is fastened to the bottom plate 43 of the apparatus, an outer guide rail 44 which, at its lower end, is fastened to the guide element 40, and a forward guide rail 45 which is also fastened to the guide element 40 at its lower end. In their upper end region, the guide rails 42, 44, 45 are maintained in the correct relative position by means of an annular plate element 46, as shown in FIG. 1. The guide rails have such a height that the slides magazine simultaneously may receive e.g. four cassettes.

The cassettes 2 in the illustrated embodiment are of a commercially available type having a design which appears best from FIG. 1 wherein the cassettes have an end opening for the introduction of microscope slides, and are provided with internal ribs (not shown) having intermediate grooves for receiving 24 mutually spaced slides 26 placed above each other. Along the outer side of the end wall located opposite to the end opening, the cassettes are provided with a number of teeth 47, more specifically 24 teeth having a mutual distance equal to the distance between the slides 26, for cooperation with a pawl means 50 for downwards feeding of the cassettes 2 in the magazine 1 in steps corresponding to the distance between the slides.

The pawl means 50 comprises a pair of pawl arms 51, 52 having a respective tooth 53, 54 for alternating engagement with the teeth 47 of the cassette, the pawl teeth 53, 54 having a height difference equal to half a tooth pitch relative to the teeth 47. The pawl arms 51, 52 are provided with a pair of oblong holes 55, 56 for slidable mounting of guide bolts 57, 58, and are moved alternatingly in the direction towards and away from the cassette teeth 47 by means of a rotary magnet 59 which is coupled to the pawl arms through a carrier hub 60 and a pair of carrier pins 61, 62 which are in slidable engagement in transversely extending grooves in the pawl arms. Such as will be seen when considering FIG. 4, the topical cassette 2 is fed down in two steps with a to-and-fro rotation of the rotary magnet, that is, in total a step corresponding to the distance between the microscope slides in the cassette.

Figure 4:
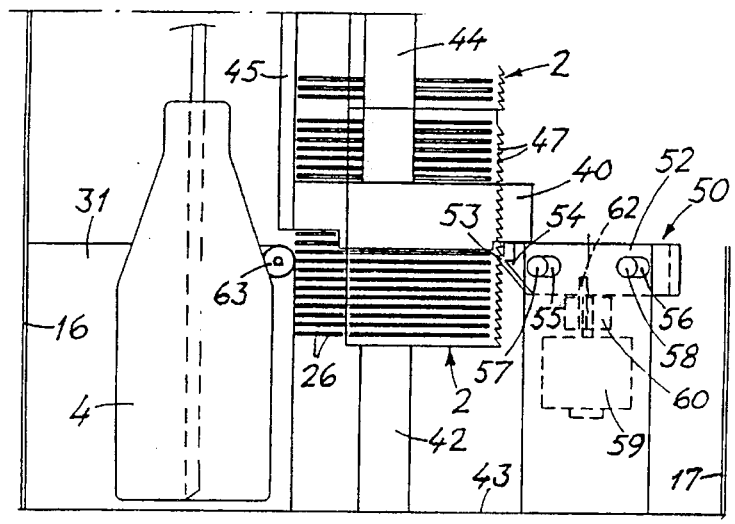
FIG. 4 shows a side view of a detail of the apparatus, more specifically the slides magazine and the means thereof for step-by-step downwards feeding of a cassette in the magazine.

As appears from FIG. 4, a roller 63 is mounted at the forward free edge of the sliding rest 31. The roller is arranged so as to have a horizontal tangent coinciding with the horizontal surface of the sliding rest 31, and a vertical tangent coinciding with the vertical edge surface of the sliding rest against which the forward ends of the slides 26 abut below the surface level of the sliding rest. In their stationary feed position, the cassettes 2 are at a level at which the topical microscope slide which is to be pulled onto the sliding rest 31, is located somewhat (approx. ½ mm) below the surface level of the sliding rest. This is to ensure that a slide, when returned from the sliding rest and into the cassette, is introduced between the supporting ribs of the cassette and does not knock against these. The roller 63 thus will assist the horizontal introduction of the microscope slides 26 onto the sliding rest 31, and will also ensure that a returned slide is brought correctly in place in the cassette when this is moved step by step downwards.

As regards the clamping arm 28 of the slide means, this is also arranged to sense whether a microscope slide is present in the topical position in the cassette 2. If a slide is not present, the clamping arm will, under the influence of the spring 29, pivot to a position wherein it actuates a microswitch 35. Activation of the microswitch results in that the slide motor 19 is reversed and brings the slide means 10 back to the initial position, at the same as the cassette is fed down one step, as described above.

The construction of the cover-slips magazine 3 appears from FIG. 8 compared with FIGS. 2 and 3. The magazine comprises a frame member 70 which is adapted to receive a stack 36 of cover slips 27 and which, in a spring-loaded manner, is supported by the slide plate 11 for tight abutment against the upper side thereof. The aforementioned recess 33 in the slide plate has such a position that it coincides with the frame member 70 when the slide means 10 is in its initial position, so that the lowermost cover slip in the stack 36 will fall into the recess 33 when the slide means is in its initial position. The depth of the recess is somewhat larger than the thickness of a cover slip, but less than the double thickness, for example 0,2 mm with a cover slip thickness of 0,15 mm. Consequently, as appears from the details A and B in FIG. 8, also the second cover slip from the bottom of the stack is located partly below the surface of the slide plate 11. At the rearward edge of the cover-slips magazine 3, the slide plate 11 is, however, provided with a chamfer 71, i.e. the rearward edge of the recess 33 is somewhat bevelled, so that the second cover slip from the bottom slides along the chamfer and onto the slide plate 11 when this is moved in the feeding direction. In this manner it is obtained that only the lowermost cover slip in the stack 36 is carried along by the slide means 10 when this is moved in the feeding direction.

In practice it may occur that the cover-slips magazine 3 with feeding movement of the slide means 10 will be forced to follow the slide means because of the fact that the two lowermost cover slips in the stack 36 adhere to each other, or because of a cover slip which has wedged itself between the recess 33 and the magazine wall. In order to allow such a movement, there is provided a spring 72 which normally keeps the magazine 3 in place, but which permits a movement of the magazine in case of failure in the cover slip supply. Further, there is provided a microswitch 73 which is activated by movement of the magazine, and which then sees to it that the slide means 10 moves back to the initial position, and further effects illumination of the red warning lamp 8 which gives a warning that the cover-slips magazine 3 should be checked.

As shown in FIGS. 2 and 3, the recess 33 of the slide plate 11 is provided with a number of slot-shaped openings 74 for escape of glass powder or possible glass particles or glass morsels from damaged cover slips.

Figure 5:
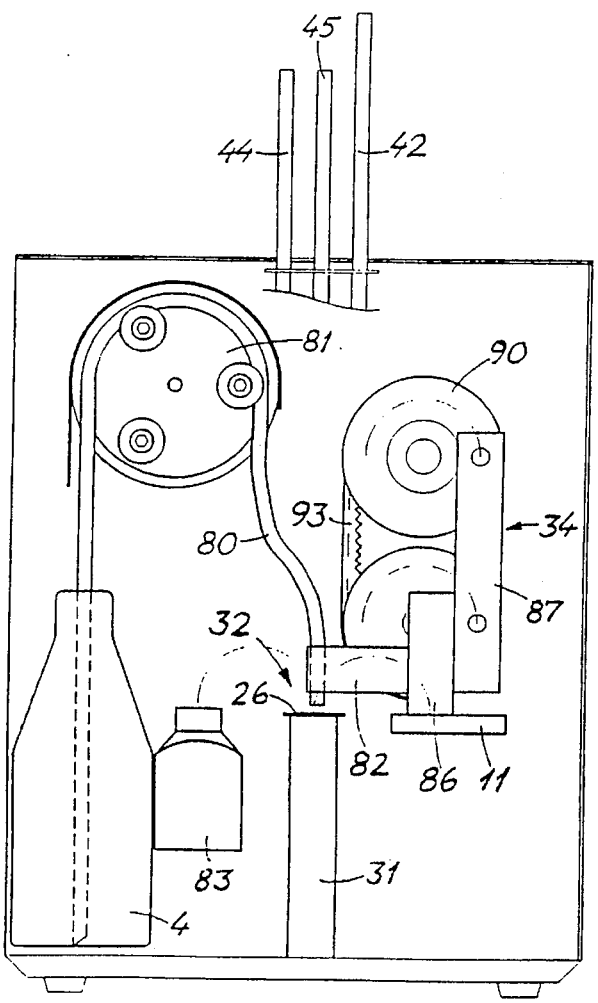
FIG. 5 shows a schematic front view of the station and the means for adhesive application, and of a fetching means for lifting, transfer and pressing-down of cover slips, the fetching means being shown in its fetching position.
Figure 6:
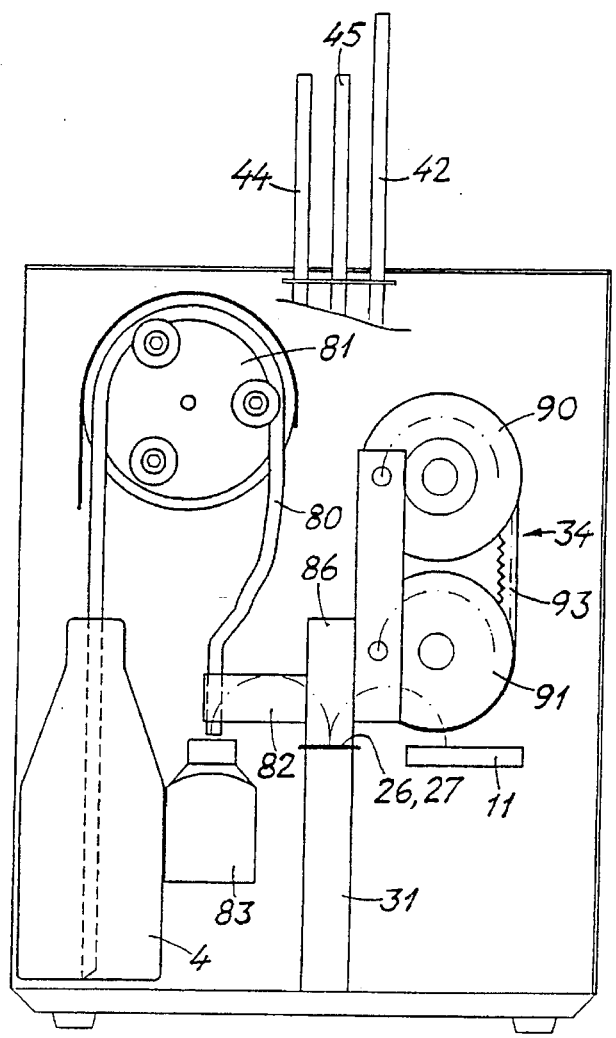
FIG. 6 shows a front view corresponding to FIG. 5, but of the fetching means shown in the pressing-down position.

FIGS. 5 and 6 show a schematic front view of the means at the adhesive application station 32 and of the fetching means 34 for lifting, transfer and pressing-down of cover slips. The bottle 4 for adhesive is placed next to the sliding rest 31. An adhesive hose 80 extends from the bottom of the bottle 4 forwards to the area of the application station 31, and is connected to a pump 81 for feeding of suitable adhesive dosis when adhesive is to be applied to slides 26. The shown pump 81 is a peristaltic pump which is fastened to the apparatus housing wall 16 and is driven by a pump motor (not shown) at the rear of the wall. Even if there is shown only one adhesive hose 80, two or more hoses may be arranged if desired, in order to distribute the adhesive on the slides. The adhesive possibly may be mixed with a suitable solvent, if this is necessary in connection with the specimens on the slides.

As shown in FIGS. 5 and 6, the outlet portion of the adhesive hose 80 is coupled to the fetching means 34 by means of a holding block 82, so that the hose follows the movements of the fetching means. Thus, the outlet portion of the hose 80 is moved between the actual application position over the microscope slides and a position wherein the mouth of the hose is located over the mouth of a drip container 83 for receiving possible adhesive drops from the hose. Advantageously, the drip container contains an exhaust-gas free liquid for receiving possible gases given off from the adhesive mixture.

The fetching means 34 of the apparatus is shown more in detail in FIGS. 7 and 8. The means serves to fetch or transfer cover slips 27 from the slide plate recess 33 to the adhesive application station 32, and to press down the cover slips in the correct position on the microscope slides after that adhesive has been applied thereto. For gripping and lifting of cover slips, the means comprises a pair of suction cups 84, 85 which are mounted in a fetching block 86 and through a non-illustrated hose connection is connected to a pneumatic drive system. The fetching block 86 is fastened to a transfer member 87 which is mounted on a pair of shaft journals or pivots 88, 89 which are fastened to the circumferential region of a driving wheel 90 and a carrier wheel 91, respectively. For stable support the carrier wheel 91 is provided with an additional support member 92 for fastening of the shaft 89. The wheels 90 and 91 are toothed wheels which are interconnected by means of a toothed belt 93. The driving wheel 90 is driven by a motor 94 through a friction coupling 95. By means of this structure there is obtained a safe and precise transfer and pressing-down of the cover slips, these being lifted and pressed down exactly vertically and during the transfer all the time maintain the same position in the space.

The pair of suction cups 84, 85 are mounted with a suitable mutual spacing in order to grip and retain the end portions of a cover slip, and between and outside of the suction cups there is arranged a downwards convexly curved abutment surface which, in the illustrated embodiment, is a plate 96 of resilient strip steel which, in its central area, is influenced by an adjustable spring 97. When activating the suction cups, these pull an underlying cover slip up to a slightly curved position in abutment against the plate 96. This arrangement provides for an efficient rolling-out of the adhesive and a safe removal of air bubbles or traces of air when the cover slips are pressed down against the microscope slides.

As an alternative to the above-mentioned embodiment, the suction cups may be arranged at different heights, so that the cover slip is kept in a slightly inclined position during the mounting.

Figure 7A:
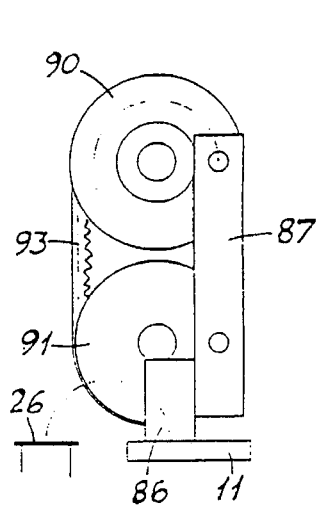
FIGS. 7A, 7B and 7C show the fetching means in the three main positions thereof, i.e. the fetching position, an intermediate position and the pressing-down position.
Figure 7B:
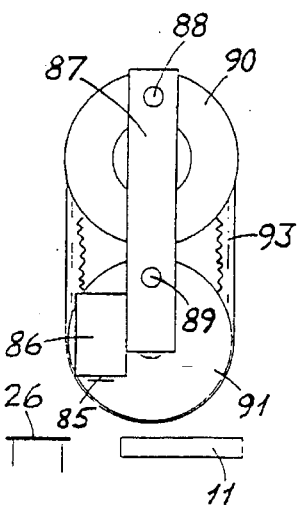
Figure 7C:
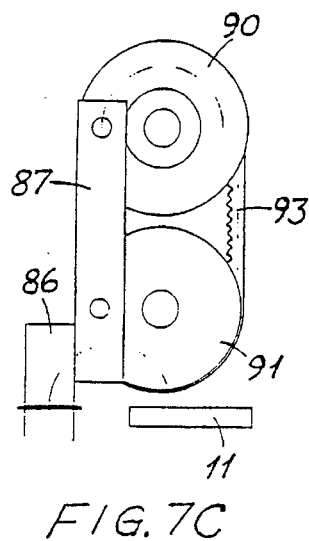

FIGS. 7A–7C show the three main positions of the fetching means, i.e. the fetching position in FIG. 7A, an intermediate position in FIG. 7B, and a pressing-down position in FIG. 7C. The intermediate position is the starting or initial position of the fetching means and is also the position assumed by the means in order to allow return of the slide means 10.

The pneumatic system of the fetching means is schematically shown in FIG. 9, compared with FIGS. 2 and 3. As shown in FIGS. 2 and 3, there is arranged a cylinder/piston unit 100 having a piston rod 101 which is coupled to the slide means 10, more specifically through an extension of the bearing holder 14 in the shown embodiment. Thus, the feeding movement of the slide means causes generation of an underpressure and an overpressure, respectively, in cylinder chambers 102 and 103 (see FIG. 9) at respective sides of the cylinder piston 104. The underpressure chamber 102 is connected to a first solenoid valve 105, and the overpressure chamber 103 is connected to a second solenoid valve 106 through an expansion chamber 107 seeing to it that a suitable overpressure (e.g. 1¼ atmosphere) is obtained in the overpressure chamber. The valves are connected in parallel with the two suction cups 84, 85 through a hose connection 108, and a vacuum switch 109 is also connected in the line 108. The mode of operation of the system will be described in connection with the later description of the mode of operation of the apparatus.

Figure 10:
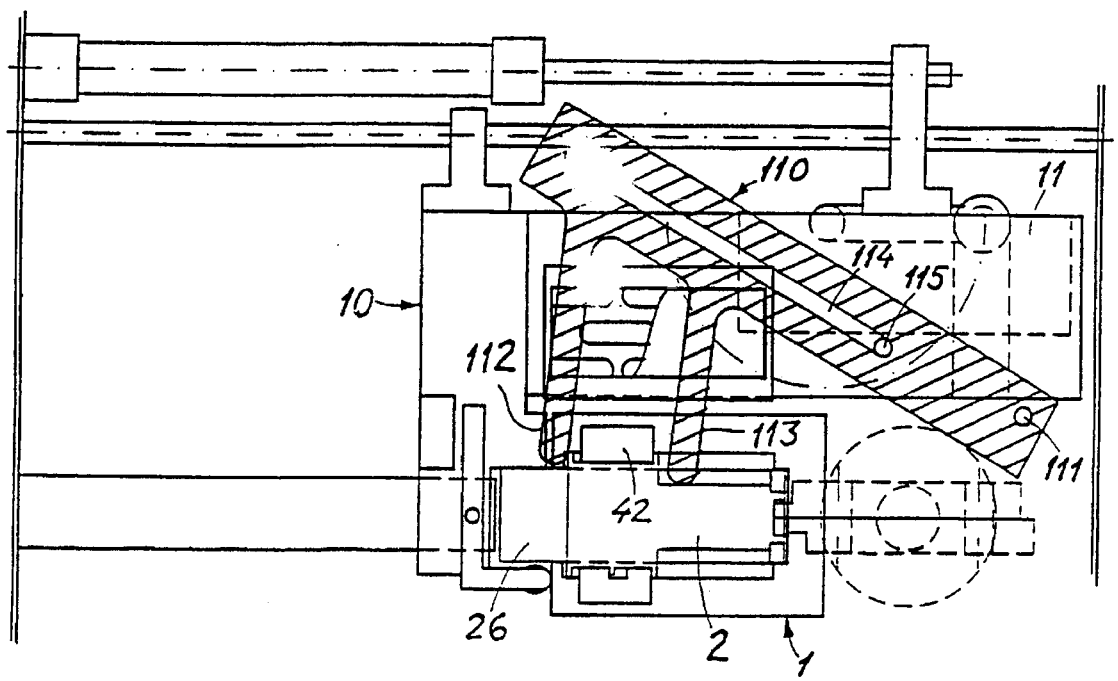
FIGS. 10 and 11 show plan views corresponding to FIGS. 2 and 3, but wherein there is shown an ejector member which, with movement of the slide means, slides out and in at a bottom plate of the apparatus, and which provides for ejection of a filled cassette when this has been dropped from the slides magazine and rests on the bottom plate.
Figure 11:
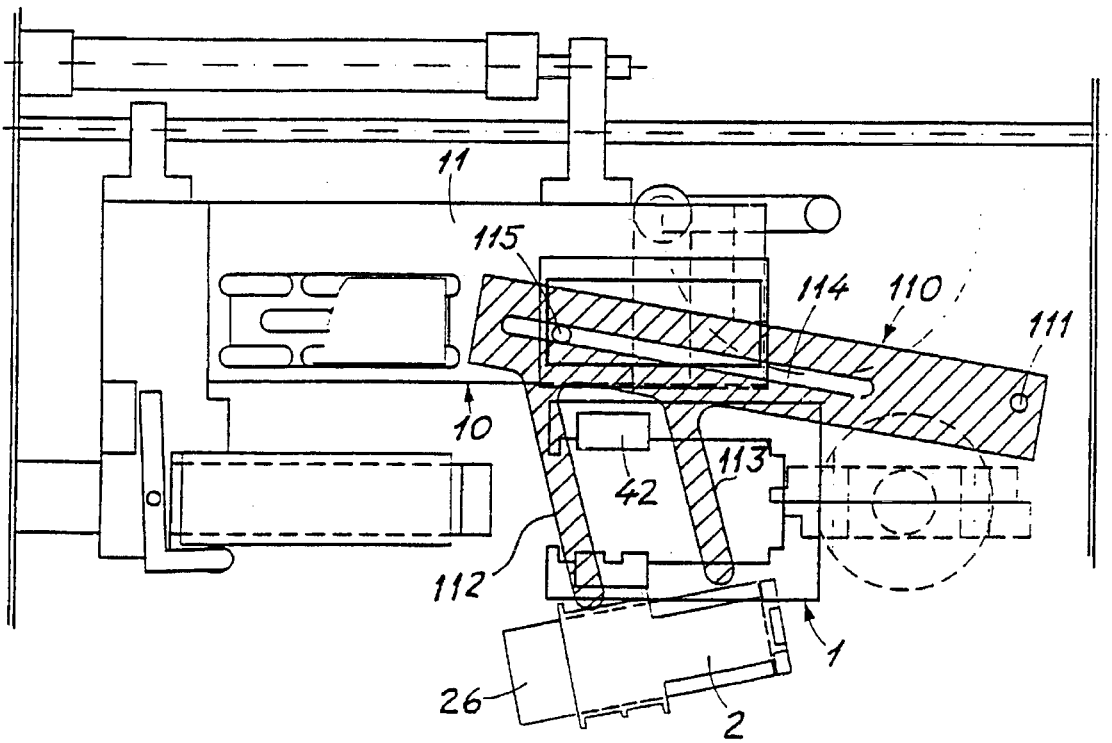

FIGS. 10 and 11 (which incidentally correspond to FIGS. 2 and 3) show an ejector means for feeding out filled cassettes 2 from the apparatus as these are dropped down from the slides magazine 1 when they are filled with finished slides. The device comprises an ejector member or ejector fork 110 consisting of a plate-shaped arm resting on the bottom plate 43 of the apparatus and being pivotally mounted by means of a pivot 111, to swing out and in controlled by the movement of the slide means 10. (The ejector member 110 in these figures is shown with solid lines and hatched to appear clearly, even if this member in the reality is only partly visible in the topical plan views.) The arm is provided with a pair of fork arms 112, 113 projecting forwards from the free end of the arm and being located on either side of the inner guide rail 42 of the slides magazine 1. Further, the arm is provided with a longitudinally extending guide slot 114 in which there engages a carrier pin 115 which is fastened to and projects vertically downwards from the slide plate 11. Thus, the ejector fork will swing outwards and inwards with each reciprocating movement of the slide means 10. For each cycle movement of the slide means, the ejector fork 110 will swing out without hitting a cassette 2 as long as the cassette is being moved down step by step in the magazine. Firstly when the cassette falls down onto the bottom plate, the ejector fork will push the cassette out, and this cassette will push the former ejected cassette in front of it. This will repeat itself until all cassettes for which there is room in the magazine (e.g. four), stand next to each other on the bottom plate.

For functional check of the apparatus according to the invention, and for control of the sequence of the working operations of the apparatus, this is provided with a programmable logic control unit (PLC unit). This unit, which is suggested symbolically with dashed lines at 75 in FIG. 1, receives control signals and acknowledgement signals from i.a. the aforementioned microswitches 35 and 73, from the vacuum switch 109, and from other acknowledgement elements (limit switches) forming part of the apparatus. These elements, and their cooperation with the PLC unit, are not further shown and described, this arrangement being of professional kind, so that a person skilled in the art may provide for the necessary arrangement according to the topical requirements.

The mode of operation of the present apparatus will be further described below.

The slide motor 19 runs the slide means 10 back and forth, a cover slip 27 in each advancing movement being carried along in the recess 33 in the slide plate 11. In the initial position of the slide means, the clamping arm 28 is forced to open position and is ready for pulling with it a microscope slide 26 from the topical position in the slides cassette 2. When the slide means 10 goes out, the clamping arm 28 is pressed to engagement with the microscope slide which is pulled out parallel to the cover slip in the recess 33, and the glasses are moved to the advanced position with correct lateral adjustment relative to each other. If there is no microscope slide in the topical position in the cassette, the clamping arm 28 will sense this and actuate the microswitch 35 as the feeding movement of the slide means starts. Thereafter, the slide means returns to the initial position, and the cassette 2 is moved down one step for another attempt to pull out a microscope slide.

During the feeding movement of the slide means, also the piston rod 101 is pushed into the cylinder 100, so that an underpressure is generated in the chamber 102 and a overpressure is generated in the chambers 103, 107, both valves 105 and 106 being closed.

The motor 94 of the fetching means 34 brings the fetching means to the fetching position wherein the mouth of the adhesive hose 80 is located just above the advanced microscope slide 26 for adhesive application, and the suction cups 84, 85 are in position for gripping the cover slip 27 in the recess 33. The valve 105 is opened for vacuum to the suction cups which attract the cover slip. This is acknowledged with a signal to the PLC unit from the vacuum switch 109.

If no cover slip is present in the recess (the magazine is empty), the fetching motor 94 goes to the intermediate position to bring the fetching means clear of the slide means, and the slide means returns to the initial position and warns about the empty magazine (the red lamp 8 lights). On the other hand, if a vacuum is obtained, the motor for the adhesive pump 81 will start, so that a suitable batch of adhesive is pumped out from the hose 80. Thereafter the cover slip is lifted over to the microscope slide and is pressed down in a slightly curved position towards the adhesive which is rolled out smoothly as the cover slip is pressed down to planar contact with the microscope slide. In this position of the fetching means, the mouth of the adhesive hose will be located above the drip container 83 which takes up drip (and also adhesive pumped out with exchange of adhesive bottle). Thereafter, the valve 105 is closed, and the valve 106 for overpressure opens so that the suction cups 84, 85 effectively drop the cover slip when they are lifted up to the intermediate position.

The slide means thereafter returns to the initial position, the means pushing back the microscope slide 26 with the attached cover slip 27 to the same position in the cassette 2. At the same time a new cover slip falls down from the cover-slips stack 36 into the recess 33. Thereafter the cassette 2 is moved down one step by means of the pawl means 50. When the last cassette has been dropped from the slides magazine, the machine stops.

I claim:

1. An apparatus for automatically attaching cover slips (27) to microscope slides (26) having specimens for microscopic examination comprising a first magazine (1) receiving a plurality of slides (26), a means (10) for feeding one slide (26) at a time from the magazine (1) to a station (32) for application of adhesive, a fetching means (34) for placing a cover slip on a slide provided with adhesive, and a means for removing the slide with attached cover slip from the station, CHARACTERIZED IN that the apparatus further comprises an additional magazine (3) arranged next to the slides magazine (1) and arranged to receive a stack (36) of cover slips (27), a slide means (10) arranged for reciprocating movement and provided with means (28, 33) for simultaneous feeding of a slide (26) and a cover slip (27) from the respective magazines (1, 3) to a position next to each other at the adhesive application station (32), and for subsequent removal of the slide with attached cover slip from the station, and wherein said fetching means (34), provided that a cover slip (27) has been fed to said position, provides for application of adhesive to the slide (26) and thereafter lifting, transfer and pressing-down of the cover slip (27) onto the slide.

2. An apparatus according to claim 1, CHARACTERIZED IN that the slides magazine (1) comprises at least one cassette (2) which is slidable along vertical guide rails (42, 44, 45), the cassette being of the type containing mutually spaced slides (26) placed above each other, and being provided along a side wall with a number of teeth (47) for cooperation with a pawl means (50) for downward movement of the cassette (2) in steps corresponding to the distance between the slides.

3. An apparatus according to claim 2, CHARACTERIZED IN that the feeding means of the slide means (10) for slides (26) comprises a sensing means (28, 35) for sensing whether a slide (26) is present in the topical position in the cassette (2), and which, in case of a lacking slide, actuates a switch (35) causing return of the slide means (10) to the initial position and one step moving-down of the topical cassette (2).

4. An apparatus according to claim 1, CHARACTERIZED IN that the slide means (10) is arranged to return the slide (26) with attached cover slip (27) from the station (32) to the slides magazine (1).

5. An apparatus according to claim 1, CHARACTERIZED IN that the slide means (10) in its reciprocating movement is driven by a motor means (19–25) which is arranged to move the slide means with a speed corresponding to a sine curve.

6. An apparatus according to any of the preceding claims, CHARACTERIZED IN that the cover-slips fetching means (34) comprises at least one suction cup (84, 85) which is coupled to a cylinder/piston unit (100) having a piston rod (101) which is coupled to the slide means (10), so that the movement of the slide means controls generation of an underpressure and an overpressure, respectively, in cylinder chambers (102, 103) on respective sides of the piston (104), at least one suction cup (84, 85) being coupled to the cylinder chambers (102, 103) through respective valves (105, 106).

7. An apparatus according to claim 6, CHARACTERIZED IN that the fetching means (34) comprises a pair of suction cups (84, 85) which are mounted with a suitable mutual distance in a holder (86) for retaining the end portions of a cover slip (27), a downwards convexly curved resilient abutment surface (96) being arranged between and outside of the suction cups (84, 85), so that the suction cups, when activated, pull the underlying cover slip (27) up to a slightly curved position in abutment against the resilient abutment surface.

8. An apparatus according to any one of claims 1–5, CHARACTERIZED IN that the cover-slips magazine (3) comprises a wall-forming frame member (70) surrounding a stack (36) of cover slips (27) and which is supported by the slide means (10), and that the slide means (10) has a cover-slips receiving recess (33) having a location corresponding to the cover-slips magazine (3) when the slide means (10) is in its initial position, so that the stack (36) of cover slips falls down into the recess (33) when the slide means (10) has been returned to this position, the recess having a depth which is adapted so that only the lowermost cover slip (27) in the stack (36) is carried along by the slide means (10) when this is moved in its feeding direction.

9. An apparatuses according to claim 8, CHARACTERIZED IN that the frame member (70) of the cover-slips magazine (3) is movable in the feeding direction of the slide means (10) against the force of a spring (72), and that the frame member (70) with such movement actuates a switch (73) causing the slide means (10) to return to the initial position.

10. An apparatus according to claim 8, CHARACTERIZED IN that the slide means (10) at the bottom of said recess (33) is provided with a number of openings (74) for escape of possible glass particles or glass powder.

11. An apparatus according to claim 1, further comprising a programmable, logic control unit (75) for functional check and control of the sequence of the working operations of the apparatus.

* * * * *